United States Patent [19]

Truthan

[11] Patent Number: 5,605,147
[45] Date of Patent: Feb. 25, 1997

[54] ENDOTRACHEAL TUBE INSERT WITH NEEDLELESS MEDICATION INJECTION PORT

[76] Inventor: Charles E. Truthan, 4075 Rum Run Ave. SE., Grand Rapids, Mich. 49546

[21] Appl. No.: 394,679

[22] Filed: Feb. 24, 1995

[51] Int. Cl.⁶ ................................................ A61M 15/00
[52] U.S. Cl. ........................ 128/203.12; 128/207.14; 128/207.15
[58] Field of Search ................. 128/203.12, 200.23, 128/207.14, 207.15

[56] References Cited

U.S. PATENT DOCUMENTS

| | | | |
|---|---|---|---|
| 1,534,913 | 4/1925 | Buck et al. | 251/149.7 |
| 4,510,933 | 4/1985 | Wendt et al. | 128/207.14 |
| 4,669,463 | 6/1987 | McConnell | 128/207.14 |
| 4,953,547 | 9/1990 | Poole, Jr. | 128/203.12 |
| 5,078,131 | 1/1992 | Foley | 128/203.15 |
| 5,119,807 | 6/1992 | Roberts | 128/200.24 |
| 5,158,569 | 10/1992 | Strickland et al. | 128/207.14 |
| 5,178,138 | 1/1993 | Walstrom | 128/200.23 |
| 5,181,508 | 1/1993 | Poole, Jr. | 128/203.12 |
| 5,207,220 | 5/1993 | Long | 128/207.14 |
| 5,231,983 | 8/1993 | Matson | 128/207.14 |
| 5,297,543 | 3/1994 | Larson | 128/200.23 |

Primary Examiner—Aaron J. Lewis
Attorney, Agent, or Firm—Van Dyke, Gardner, Linn & Burkhart, LLP

[57] ABSTRACT

This device allows for the rapid administration of liquid medicants into the lungs of a patient via endotracheal tube (34) without interrupting the ventilation cycles and without the risk of displacement of endotracheal tube (34) from the patient. An endotracheal insert apparatus (32) that consists of: ventilation adaptor apparatus (10), inserted between endotracheal tube (34) and the means for ventilation of the patient; medication injection apparatus (18); and medication tubing (24A), that is inserted down endotracheal tube (34). A syringe without needle is attached to medication injection apparatus (18) at twist lock adaptor (20). The liquid medicant is then forced from the syringe and travels thru medication tubing (24) and medication tubing (24A) and expelled at the distal end of endotracheal tube (34) thru ejection port (28). In one alternative embodiment, the addition of collapsible sheath (30) allows for the retraction of medication tubing (24B) from endotracheal tube (34) when medication is not being injected.

18 Claims, 2 Drawing Sheets

ENDOTRACHEAL TUBE INSERT WITH NEEDLELESS MEDICATION INJECTION PORT

CROSS REFERENCES TO RELATED APPLICATIONS

The invention of this application is related and complimentary to my copending application filed 6 Feb. 1995, titled SYRINGE FOR THE MIXING OF MEDICANTS THEN INJECTION VIA THE ENDOTRACHEAL TUBE.

BACKGROUND—FIELD OF INVENTION

This invention relates to the field of medicine, specifically to an endotracheal tube insert apparatus that is capable of rapidly delivering liquid medicants down an endotracheal tube, via needleless injection, to the lungs.

BACKGROUND—DESCRIPTION OF PRIOR ART

Endotracheal tubes are placed thru the nose or mouth and into the trachea of the lungs. The endotracheal tube "secures" the airway during medical emergencies and surgeries. The endotracheal tube prevents aspiration of gastric contents into the lungs. The endotracheal tube provides direct access to the lungs for ventilation and exchange of gasses (Oxygen and Carbon Dioxide, etc.).

In an emergency or during surgery, the preferred route for administering medications is thru an intravenous (IV) catheter. Frequently, there is either a delay in obtaining that IV access or all IV sites are in use with other medicines.

Some medications (such as Narcan, Atropine, Valium, Epinephrine, Lidocaine, and the like) can be administered down the endotracheal tube and absorbed by the blood vessels in the lungs, or pulmonary vasculature, and from there into the heart and the systemic vasculature. When administered via the lungs, the medicine is required to be two to two and one half times the IV dose and diluted in ten cc of normal saline or sterile water.

The current methods of administering medication via the lungs require stopping breathing, disconnecting the bag valve device (or other mechanical breathing device), inserting a smaller tube down the endotracheal tube and "squirting" the medicine thru the smaller tube (or directly into the endotracheal tube), reconnecting the bag valve device or other breathing device and resuming breathing. This consumes excessive time, does not aerosolize the medicine (for best dispersement to the most lung surface area for optimal absorption), and, every time the endotracheal tube is manipulated by connecting and disconnecting the breathing device, there is the risk of relocationg the endotracheal tube to a suboptimal location, including the complete displacement of it from the trachea. Further, in the blind passing of a catheter down the endotracheal tube, it is possible to pass the catheter only into one lung and therefore not get optimal distribution of the medication. If the medication is administered at the proximal end of the endotracheal tube, much of it will adhere to the wall of the tube itself and therefore not be available for absorption in the lungs.

U.S. Pat. No. 5,078,131 to Foley, Martin P (Jan. 7, 1992) is for the administration of a metered dose inhaler (MDI) canister medicant, not a liquid medicant into the lungs via the endotracheal tube.

U.S. Pat. No. 4,953,547 to Poole Jr., Samuel E. (Sep. 4, 1990) uses a resealable needle injector port on an apparatus that replaces the universal adaptor on the proximal end of the endotracheal tube. Medicant is then injected into this adaptor and carried down the endotracheal tube to the distal end by gravity, airflow etc. Medicant will adhere to the endotracheal tube wall from proximal to distal end.

U.S. Pat. No. 5,119,807 to Roberts, Josephine A.; Burwell, Jephthae W. (Jun. 9, 1992) is designed for use on a closed ventilator system and allows for the nebulization of medicants and the removal of condensation from the ventilator circuit or tubing. It is not designed for the emergency administration of medicants rapidly. It is not adaptable for field and emergency room usage.

U.S. Pat. No. 5,178,138 to Walstrom, Dennis R.; Maslonka, Steven R.; Scoles, Wade J. (Jan. 12, 1993) is a spacer device so that a metered dose inhaler medication can be given to a patient on a ventilator.

U.S. Pat. No. 5,207,220 to Long, Walker A. (May 4, 1993) is a method for the administration of medicants to the lungs, designed for the slow injection of medication so as to trickle down the tube and into the selected lung. It is intended to pass medicants that coat the surface of the lung, are not absorbed, and not for rapid emergency administration of medicants.

U.S. Pat. No. 5,231,983 to Matson, Charles J.; Velasquez, David J. (Aug. 3, 1993) is a device that allows for the aerosolization of liquid medicants by an aerosolizing spray bar that crosses the internal diameter of the endotracheal tube. The spray bar is incorporated within the main air lumen of the endotracheal tube. This spray bar will block the passage of suction catheters and disrupts the normal air flow thru the tube.

U.S. Pat. No. 5,297,543 to Larson, Douglas A.; Danowski, Thomas J. (Mar. 29, 1994) is a device that utilizes a venturi system to mix medicant (primarily metered dose inhalers) in the pressurized intake (to patient) line of a ventilator system. It allows for a large surface area to which the medicant can adsorb and therefore not be available for absorption in the lungs of the patient.

OBJECTS AND ADVANTAGES

Accordingly, several objects and advantages of my invention are the ability to inject liquid medication into the lungs without the interruption of ventilation. No manipulation of the endotracheal tube is required and hence no risk of relocating the endotracheal tube is present. Further, the medication is dispensed near the distal end of the endotracheal tube and is therefore not adsorbed along the length of the endotracheal tube, and is distributed to both lungs. With this invention, there is no blockage to the passage of a suction catheter down the endotracheal tube. When this invention is used in conjunction with my invention SYRINGE FOR THE MIXING OF MEDICANTS THEN INJECTION VIA THE ENDOTRACHEAL TUBE, liquid medicants intended for intravenous injection can be mixed and administered thru this endotracheal tube insert and into the patient's bloodstream by absorption from the lungs.

Still further objects and advantages will become apparent from a consideration of the ensuing description and accompanying drawings.

BRIEF DESCRIPTION OF THE DRAWINGS

FIG. 3 is a perspective view of my invention placed within an endotracheal tube.

Figure 1:
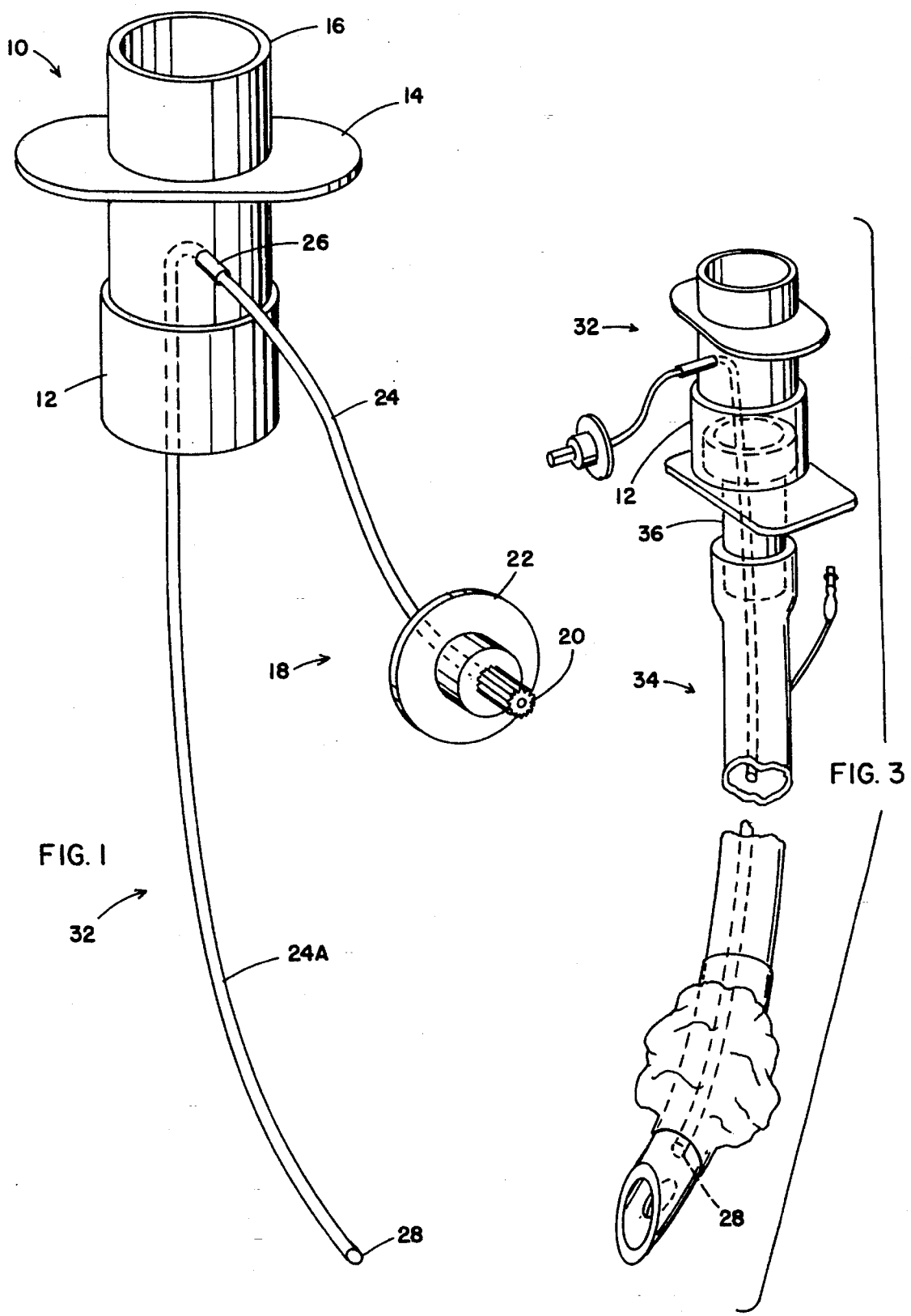
FIG. 1 is a perspective view of my invention.

REFERENCE NUMERALS 10 ventilation adaptor apparatus
12 female endotracheal adaptor
14 ventilation grip wing
16 ventilation male adaptor
18 medication injection apparatus
20 twist lock adaptor
22 medication grip wing
24 medication tubing
24A medication tubing
24B medication tubing
26 connection
26A connection
26B connection
28 ejection port
28A ejection port
30 collapsible sheath
32 endotracheal insert apparatus
34 endotracheal tube
36 endotracheal tube male adaptor
38 stopper
40 protrusion

SUMMARY

An endotracheal tube insert apparatus coupleable to a needleless syringe containing liquid medicant comprising: a rigid, tubular ventilation adaptor apparatus having a proximal ventilation male adaptor end and a distal female endotracheal adaptor end; a medication injection apparatus having a twist lock adaptor and backcheck valve; a flexible medication tubing connecting the medication injection apparatus to the ventilation adaptor apparatus; a generally elongated, semirigid medication tubing starting from a connection within the ventilation adaptor apparatus and exiting thru the female endotracheal adaptor end; the semirigid medication tubing being of sufficient length to extend to but not past the distal end of an endotracheal tube and terminating in an ejection port; whereby, after an endotracheal tube has been passed into the air passageways of a patient, the endotracheal tube insert apparatus is inserted into the endotracheal tube by passing the semirigid medication tubing thru the air passage lumen of the endotracheal tube and attaching the female endotracheal adaptor to the endotracheal tube's male adaptor, and while applying a breathable gas to the ventilation male adaptor of the ventilation adaptor apparatus, and therefore into the endotracheal tube and to the patient, a needleless syringe containing liquid medicant is attached to the twist lock adaptor and effecting a pumping action on the syringe, the liquid medicant is positively forced thru the backcheck valve, into the flexible medication tubing, to and thru the connection within the ventilation adaptor apparatus then thru the semirigid medication tubing and discharged at the ejection port within the distal end of the endotracheal tube and therefrom absorbed through the walls of the lungs and into the bloodstream of the patient.

PREFERRED EMBODIMENT—DESCRIPTION

FIG. 1. shows my endotracheal insert apparatus 32 in its' basic form. It consists of a ventilation adaptor apparatus 10 comprised of female endotracheal adaptor 12, ventilation grip wing 14, and ventilation male adaptor 16, to which is attached the means of ventilating the patient. Medication injection apparatus 18 consists of twist lock adaptor 20 connected to medication tubing 24 with medication grip wing 22 provided for ease of holding medication injection apparatus 18. Twist lock adaptor 20 has a backcheck valve included to prevent the backflow of gasses and medicant. Backcheck valves have been described elsewhere and are well known in the field. Medication tubing 24 enters ventilation adaptor apparatus 10 at connection 26 with medication tubing 24A exiting ventilation adaptor apparatus 10 thru female endotracheal adaptor 12 terminating at ejection port 28. However, it is to be understood that applicant's invention is not limited to the angle of attachment nor the exact location of attachment of connection 26 on ventilation adaptor apparatus 10. Further, it is to be understood that applicant's invention is not limited to the exact style nor the inclusion of ventilation grip wing 14 and, or medication grip wing 22.

Figures 2, 4:
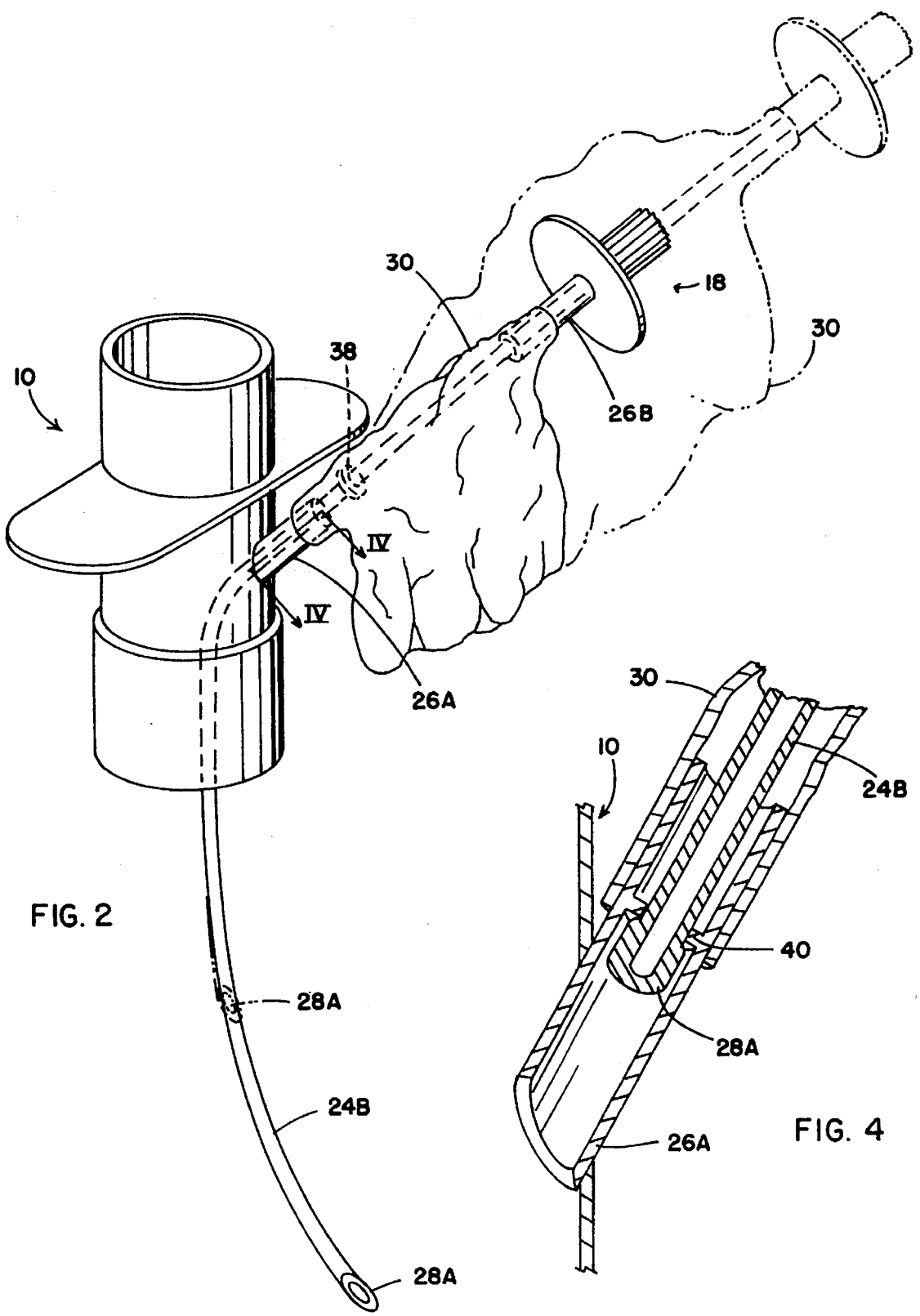
FIG. 2 is a perspective view of my invention with a collapsible sheath enveloping a retractable medication tubing 24B.
FIG. 4 is a sectional view in detail of the portion indicated by section lines 4—4 in FIG. 2 with medication tubing 24B in the retracted position.

FIG. 2. shows one alternative endotracheal insert that includes a collapsible sheath 30. Collapsible sheath 30 attaches to ventilation adaptor apparatus 10 at connection 26A and to medication injection apparatus 18 at connection 26B. Medication tubing 24B attaches to medication injection apparatus 18 is enclosed within collapsible sheath 30 and freely moveable thru connection 26A. Ejection port 28A is flared to prevent retraction past connection 26A. Medication tubing 24B has a stopper 38, attached to prevent the complete extension of medication tubing 24B. However, it is to be understood that applicant's invention is not limited to the angle of attachment nor the exact location of attachment of connection 26A on ventilation adaptor apparatus 10. Further, it is to be understood that applicant's invention is not limited to the exact style of collapsible sheath 30. It is further understood that the applicant's invention is not limited to the exact style of flaring on ejection port 28A nor the exact style of stopper 38. Phantom lines show medication tubing 24B partially retracted and collapsible sheath 30 partially expanded.

FIG. 3. shows the basic endotracheal insert apparatus 32 as it would be attached to endotracheal tube 34, with female endotracheal adaptor 12 fitting over and attaching to endotracheal tube male adaptor 36. It shows the approximate location of ejection port 28 near the distal tip of endotracheal tube 34.

FIG. 4. shows a sectional view taken along section lines 4—4 of FIG. 2. It shows medication tubing 24B retracted with the flared end of ejection port 28A stopped by protrusion 40 within connection 26A. However, it is to be understood that applicant's invention is not limited to the exact style or design of the flare of ejection port 28A nor protrusion 40 within connection 26A, but any design that prevents the complete retraction of medication tubing 24B within collapsible sheath 30 is acceptable.

PREFERRED EMBODIMENT—OPERATION

Operation and use of the insert is simple and straight forward. Ventilation adaptor apparatus 10 is connected to endotracheal tube 34 by passing medication tubing 24A down the central air passage lumen of endotracheal tube 34 and pressing female endotracheal adaptor 12 onto endotracheal tube male adaptor 36 as shown in FIG. 3. A means for ventilating the patient is attached to ventilation male adaptor 16 and the patient can be continuously ventilated with a breathable gas. A needleless syringe filled with liquid medicant is attached to twist lock adaptor 20. A positive pumping action is applied to the syringe and the medicant is injected thru the backcheck valve of twist lock adaptor 20, thru medication tubing 24, connection 26, medication tubing 24A and discharged into the distal end of endotracheal tube 34 at ejection port 28.

In one alternative embodiment shown in FIG. 2, ventilation adaptor apparatus 10 is connected to endotracheal tube 34 at endotracheal tube male adaptor 36 as before. Medication injection apparatus 18 is unchanged. A collapsible sheath 30 is added to the insert device. Collapsible sheath 30 provides for the protection of medication tubing 24B from contaminants, such as dirt or germs. Collapsible sheath 30 and connection 26A allow medication tubing 24B to freely slide in and out of endotracheal tube 34. This retractability of medication tubing 24B permits better airflow thru endotracheal tube 34 when not injecting medication. It further allows for easier passage of a suction catheter down endotracheal tube 34 when suctioning of matter from the lungs is required. Medication tubing 24B is prevented from being withdrawn completely into collapsible sheath 30 by a flaring at ejection port 28A that is stopped by protrusion 40 within the wall of connection 26A as shown in FIG. 4. Medication tubing 24B is prevented from being extended past the distal end of endotracheal tube 34 by a stopper 38 that is stopped by protrusion 40.

Thus we can see that either of these embodiments allows for the administration of liquid medicant down an endotracheal tube without the risk of displacement of that endotracheal tube during the administration process. By discharging the medicant near the distal tip of the endotracheal tube, adsorption of medicant to the endotracheal tube is minimized.

CONCLUSIONS, RAMIFICATIONS, AND SCOPE

Accordingly, it can be seen that the invention allows for the rapid administration of liquid medicant via a prepositioned endotracheal tube 34, to the lungs of a patient while minimizing the movement of endotracheal tube 34, and hence minimal risk of displacement of endotracheal tube 34 from the patient, and allows for ventilations to continue without interruption during the medication administration process. Ventilation male adaptor 16 and female endotracheal adaptor 12 of ventilation adaptor apparatus 10 are of industry standard dimensions for connection to endotracheal tube 34 and the means for ventilation. Medication injection apparatus 18 contains a backcheck valve to prevent backflow of gas and liquid, and allows for the needleless connection of a syringe at twist lock adaptor 20 and the rapid injection of liquid medicant to the lungs of the patient. The liquid medicant is carried thru medication tubing 24 and medication tubing 24A and expelled into the distal end of endotracheal tube 34 at ejection port 28, thereby minimizing the adsorption of medicant to the walls of endotracheal tube 34. In the other shown embodiment, collapsible sheath 30 allows for the complete retraction of medication tubing 24B from the air passage lumen of endotracheal tube 34 and thereby eliminates any reduction and resistance to air flow produced by medication tubing 24B.

Although the description above contains many specificities, these should not be construed as limiting the scope of the invention but as merely providing illustrations of some of the presently preferred embodiments of this invention. Various other embodiments and ramifications are possible within it's scope. For example, the insert can be made to fit any hollow tubular probe and used for passage of any fluid or gas while minimizing the movement of that probe. Instead of a needleless twist lock adaptor 20, a resealable port could be substituted so that a needle punctures the port and medicant is then injected. Instead of an open end at ejection port 28 or ejection port 28A, a "shower head" type end could be integrated to better aerosolize the medicant into the air stream. An additional port could be added to ventilation adaptor apparatus 10 for the passage of a suction catheter down endotracheal tube 34 without disconnecting the means of ventilation. In yet another embodiment, female endotracheal adaptor 12 could be replaced with a tapered universal endotracheal tube adaptor and thereby eliminate endotracheal tube male adaptor 36 that is supplied with each endotracheal tube 34.

Thus the scope of the invention should be determined by the appended claims and their legal equivalents, rather than by the examples given.

What is claimed is:

1. An endotracheal tube insert apparatus coupleable to a syringe containing liquid medicant comprising:

a rigid, tubular ventilation adaptor apparatus having a proximal ventilation adaptor end and a distal endotracheal adaptor;

a medication injection apparatus and a flexible medication tubing connecting said medication injection apparatus to said ventilation adaptor apparatus;

a generally elongated, semirigid medication tubing starting from a connection within said ventilation adaptor apparatus and exiting thru said endotracheal adaptor;

said semirigid medication tubing being of sufficient length to extend to a distal end of an endotracheal tube without extending past the endotracheal tube distal end and terminating in an ejection port;

a collapsible sheath attached to said medication injection apparatus and to said ventilation adaptor apparatus;

wherein said semirigid medication tubing freely passes thru said connection of said ventilation adaptor apparatus and connects with said medication injection apparatus;

wherein said ejection port can not be withdrawn past said connection of said ventilation adaptor apparatus; and said semirigid medication tubing including a stopper positioned between said connection and said medication injection apparatus that can not be extended past said connection of said ventilation adaptor apparatus thereby preventing said ejection port from extending past an endotracheal tube distal end;

wherein said collapsible sheath surrounds said semirigid medication tubing between said ventilation adaptor apparatus and said medication injection apparatus;

wherein said collapsible sheath provides protection from contamination of said semirigid medication tubing;

whereby, pulling on said medication injection apparatus said semirigid medication tubing can be withdrawn from an endotracheal tube air passage lumen, protected by said collapsible sheath and reinserted, by pushing on said medication injection apparatus, into an endotracheal tube air passage lumen as needed for the injection of additional said liquid medicant, without disconnecting and removing said endotracheal tube insert apparatus from such endotracheal tube.

2. An endotracheal tube insert apparatus as set forth in claim 1 including a medication grip wing on said medication injection apparatus.

3. An endotracheal tube insert apparatus as set forth in claim 1 including a ventilation grip wing on said ventilation adaptor apparatus.

4. An endotracheal tube insert apparatus as set forth in claim 1 including a closeable port on said ventilation adaptor apparatus for the passage of a suction catheter down said endotracheal tube.

5. An endotracheal tube insert apparatus as set forth in claim 1 wherein said ejection port has a plurality of openings to promote aerosolization of said liquid medicant.

6. An endotracheal tube insert apparatus as set forth in claim 1 wherein said endotracheal adaptor is a tapered universal male adaptor wherein said ventilation adaptor apparatus can be connected directly to the endotracheal tube by said tapered universal male adaptor.

7. An endotracheal tube insert apparatus as set forth in claim 1 wherein said medication injection apparatus comprises a resealable injection port whereby a syringe with needle may be used to inject said liquid medicants.

8. The endotracheal tube insert apparatus as set forth in claim 1 wherein said medication injection apparatus comprises a twist lock adaptor and backcheck valve.

9. The endotracheal tube insert apparatus as set forth in claim 1 wherein said endotracheal adaptor comprises a female adaptor.

10. A method of administering medicine to the lungs of a patient comprising:

placing an endotracheal tube having a main air passage through the nose or mouth of a patient, through the oropharynx, between the vocal cords and into the trachea of a patient;

providing an endotracheal tube insert apparatus having a ventilation adaptor apparatus, a medication injection apparatus, a flexible medication tubing and a semirigid medication tubing, said ventilation adaptor apparatus including an endotracheal adaptor, a ventilation male and a connection for said semirigid medication tubing and said flexible medication tubing, said semirigid medication tubing having a distal end with an ejection port and being of adequate length to reach to but not pass the distal end of said endotracheal tube:

inserting said semirigid medication tubing into the main air passage lumen of said endotracheal tube and attaching said endotracheal adaptor to the endotracheal tube adaptor of said endotracheal tube and passing a breathable gas through said ventilation adaptor apparatus and said endotracheal tube to said patient, attaching a syringe filled with liquid medicant to said medication injection apparatus and effecting a pumping action on said syringe in order to positively force liquid medicant thru said flexible medication tubing, thru said connection within said ventilation adaptor apparatus, thru said semirigid medication tubing and discharging said liquid medicant at said ejection port within the distal end of said endotracheal tube to be absorbed through the walls of the lungs into the bloodstream of said patient, wherein said endotracheal tube insert apparatus includes a collapsible sheath attached to said medication injection apparatus and to said ventilation adaptor apparatus;

wherein said semirigid medication tubing freely passes thru said connection of said ventilation adaptor apparatus and connects with said medication injection apparatus, said ejection port is configured so that it can not be withdrawn past said connection of said ventilation adaptor apparatus and said semirigid medication tubing includes a stopper positioned between said connection and said medication injection apparatus that can not be extended past said connection of said ventilation adaptor apparatus thereby preventing said ejection port from extending past the distal end of said endotracheal tube;

said collapsible sheath surrounds said semirigid medication tubing between said ventilation adaptor apparatus and said medication injection apparatus providing protection from contamination of said semirigid medication tubing; and further including the step of withdrawing said medication tubing from said air passage lumen by pulling on said medication injection apparatus and reinserting said medication tubing in said air passage lumen by pushing on said medication injection apparatus as needed for the injection of additional liquid medicant, without disconnecting and removing said endotracheal tube insert apparatus from said endotracheal tube.

11. A method of administering medicine to the lungs of a patient as set forth in claim 10 wherein said endotracheal tube insert apparatus includes a medication grip wing on said medication injection apparatus.

12. A method of administering medicine to the lungs of a patient as set forth in claim 10 wherein said endotracheal tube insert apparatus includes a ventilation grip wing on said ventilation adaptor apparatus.

13. A method of administering medicine to the lungs of a patient as set forth in claim 10 wherein said endotracheal tube insert apparatus includes a closeable port on said ventilation adaptor apparatus for the passage of a suction catheter down said endotracheal tube.

14. A method of administering medicine to the lungs of a patient as set forth in claim 10 wherein said ejection port of said endotracheal tube insert apparatus has a plurality of openings to promote aerosolization of said liquid medicant.

15. A method of administering medicine to the lungs of a patient as set forth in claim 10 wherein said endotracheal adaptor comprises a tapered universal male adaptor and said step of attaching said endotracheal adaptor includes attaching said ventilation adaptor apparatus directly to said endotracheal tube by said tapered universal male adaptor.

16. A method of administering medicine to the lungs of a patient as set forth in claim 10 wherein said medication injection apparatus comprises a resealable injection port whereby a syringe with needle may be used to inject said liquid medicants.

17. The method of administering medicine to the lungs of a patient as set forth in claim 10 wherein said endotracheal adaptor comprises a female adaptor.

18. The method of administering medicine to the lungs of a patient as set forth in claim 10 wherein said medication injection apparatus comprises a twist lock adaptor and backcheck valve.

* * * * *